United States Patent
Hanaoka (10) Patent No.: US 10,912,921 B2
(45) Date of Patent: Feb. 9, 2021

(54) MULTILAYER BODY, MULTILAYER HOLLOW BODY, AND CATHETER WITH MULTILAYER HOLLOW BODY

(71) Applicant: ASAHI INTECC CO., LTD., Seto (JP)

(72) Inventor: Atsuhiro Hanaoka, Izumiotsu (JP)

(73) Assignee: ASAHI INTECC CO., LTD., Seto (JP)

(*) Notice: Subject to any disclaimer, the term of this patent is extended or adjusted under 35 U.S.C. 154(b) by 380 days.

(21) Appl. No.: 15/651,491

(22) Filed: Jul. 17, 2017

(65) Prior Publication Data
US 2018/0104440 A1 Apr. 19, 2018

Related U.S. Application Data

(63) Continuation of application No. PCT/JP2016/080345, filed on Oct. 13, 2016.

(51) Int. Cl.
A61M 25/00 (2006.01)
A61M 25/01 (2006.01)
A61M 39/10 (2006.01)

(52) U.S. Cl.
CPC ...... *A61M 25/005* (2013.01); *A61M 25/0045* (2013.01); *A61M 25/0068* (2013.01);
(Continued)

(58) Field of Classification Search
CPC ............ A61M 25/005; A61M 25/0045; A61M 25/0068; A61M 25/0105; A61M 25/0069; A61M 39/10
See application file for complete search history.

(56) References Cited

U.S. PATENT DOCUMENTS 1,905,197 A * 4/1933 Webb .................. F16C 1/02
464/58
5,052,404 A * 10/1991 Hodgson ............. A61M 25/005
267/155

(Continued)

FOREIGN PATENT DOCUMENTS

EP 2845620 A1 3/2015
JP 2000-160488 * 6/2000
(Continued)

OTHER PUBLICATIONS

Jun. 17, 2019 Office Action issued in Korean Patent Application No. 10-2017-7011396.
(Continued)

*Primary Examiner* — Theodore J Stigell
(74) *Attorney, Agent, or Firm* — Oliff PLC (57) ABSTRACT

A multilayer body, a multilayer hollow body, and a catheter with a multilayer hollow body each have improved torque transmissibility to one end when the other end is rotated rightward or leftward. The multilayer hollow body includes a single-strand hollow body that is formed by winding one element wire, an inner multi-strand hollow body that is disposed adjacently to an inner periphery of the single-strand hollow body and is formed by winding a plurality of element wires in an opposite direction from the single-strand hollow body, and an outer multi-strand hollow body that is disposed adjacently to an outer periphery of the single-strand hollow body 7 and is formed by winding a plurality of element wires in an opposite direction from the single-strand hollow body.

5 Claims, 8 Drawing Sheets

(52) U.S. Cl.
CPC ........ *A61M 25/0105* (2013.01); *A61M 39/10* (2013.01); *A61M 25/0069* (2013.01)

(56) References Cited

U.S. PATENT DOCUMENTS

| | | | | |
|---|---|---|---|---|
| 5,154,705 | A * | 10/1992 | Fleischhacker | A61B 17/3207 600/585 |
| 5,165,421 | A * | 11/1992 | Fleischhacker | A61B 17/3207 138/130 |
| 5,306,252 | A * | 4/1994 | Yutori | A61M 25/005 138/130 |
| 5,554,139 | A * | 9/1996 | Okajima | A61M 25/005 600/433 |
| 6,210,395 | B1 * | 4/2001 | Fleischhacker | A61B 17/3207 604/523 |
| 6,526,645 | B2 * | 3/2003 | Romano | A61B 17/1642 29/435 |
| 6,881,194 | B2 * | 4/2005 | Miyata | A61B 5/6851 600/585 |
| 2008/0097401 | A1 * | 4/2008 | Trapp | A61B 17/12022 604/527 |
| 2012/0004606 | A1 * | 1/2012 | Lentz | A61M 25/005 604/103.04 |
| 2016/0001040 | A1 | 1/2016 | Yamaguchi et al. | |
| 2016/0001048 | A1 * | 1/2016 | Koike | A61M 25/09 604/528 |
| 2016/0279383 | A1 * | 9/2016 | Kanazawa | A61M 25/001 |

FOREIGN PATENT DOCUMENTS

| | | |
|---|---|---|
| JP | 2000-160488 A | 6/2000 |
| JP | 2011-177231 A | 9/2011 |
| JP | 2013-085698 A | 5/2013 |
| JP | 2015-051085 A | 3/2015 |

OTHER PUBLICATIONS

Mar. 20, 2020 Decision of Rejection for Amendment issued in Korean Patent Application No. 10-2017-7011396.

* cited by examiner

MULTILAYER BODY, MULTILAYER HOLLOW BODY, AND CATHETER WITH MULTILAYER HOLLOW BODY

CROSS REFERENCE TO RELATED APPLICATION

This application is a continuation of PCT/JP2016/080345 filed on Oct. 13, 2016, the contents of which are incorporated by reference herein in their entirety.

BACKGROUND

The disclosed embodiments relate to a medical device. Specifically, the disclosed embodiments relate to a multilayer body including a plurality of concentric layers, a multilayer hollow body with a plurality of hollow bodies arranged concentrically, and a catheter with such a multilayer hollow body.

Conventionally, various multilayer bodies including a plurality of concentric layers have been used.

For example, Japanese Patent Application Laid-open No. 2000-160488 describes a multilayered and twisted spiral rope (hereinafter, referred to as a "multilayer body") in which S-twisted layers and Z-twisted layers, which are formed by S-twisting (counterclockwise twisting) or Z-twisting (clockwise twisting) a plurality of wires around a core wire, are arranged alternately in a plurality of layers (see Paragraph [0009] and FIG. 1(c), etc.).

However, in the multilayer body described in Japanese Patent Application Laid-open No. 2000-160488, the stranded wires formed of a plurality of wires are arranged in a plurality of layers around the core wire. Therefore, a stranding angle of the stranded wire in each layer is small, and when one end of the multilayer body is rotated rightward or leftward, the rotational torque transmissibility to the other end is insufficient.

This problem occurs not only in a multilayer body but also in a multilayer hollow body formed by removing a core from a multilayer body, and also occurs in a catheter using a multilayer hollow body.

SUMMARY

The disclosed embodiments have been devised to address the above-described problem, and aim to provide a multilayer body, a multilayer hollow body, and a catheter with a multilayer hollow body having improved rotational torque transmissibility to the one end when the other end is rotated rightward or leftward.

To achieve such an object, a multilayer body of the disclosed embodiments includes a single-strand hollow body that is wound by one element wire, an inner multi-strand hollow body that is disposed adjacently to an inner periphery of the single-strand hollow body and wound by a plurality of element wires in an opposite direction from the single-strand hollow body, and an outer multi-strand hollow body that is disposed adjacently to an outer periphery of the single-strand hollow body and wound by a plurality of element wires in an opposite direction from the single-strand hollow body. When one end of the multilayer body is rotated rightward or leftward, it is possible to improve the rotational torque transmissibility to the other end of the multilayer body.

The multilayer body may be a multilayer hollow body. In the multilayer hollow body, a lumen defined by an inner periphery of the inner multi-strand hollow body does not contain any solid structure. When one end of the multilayer hollow body is rotated rightward or leftward, it is possible to improve the rotational torque transmissibility to the other end of the multilayer hollow body.

Moreover, a catheter of the disclosed embodiments includes the multilayer hollow body described above, a distal end tip that is connected to a distal end of the multilayer hollow body, and a connector that is connected to a proximal end of the multilayer hollow body. When one end of the catheter is rotated rightward or leftward, it is possible to improve the rotational torque transmissibility to the other end of the catheter.

Furthermore, a catheter of the disclosed embodiments includes an inner layer, the multilayer hollow body described above disposed on an outer periphery of the inner layer, an outer layer that covers the inner layer and the multilayer hollow body, a distal end tip that includes a distal end of the multilayer hollow body inside the distal end tip and is connected to a distal end of the inner layer and a distal end of the outer layer, and a connector that is connected to a proximal end of the inner layer, a proximal end of the outer layer, and a proximal end of the multilayer hollow body. When one end of the catheter is rotated rightward or leftward, it is possible to further improve the rotational torque transmissibility to the other end of the catheter.

DETAILED DESCRIPTION OF EMBODIMENTS

Embodiments of the invention will be described with reference to the enclosed drawings. In each of FIGS. 1-4 and 6-8, the left side corresponds to a distal end, and the right side corresponds to a proximal end.

Figure 1:
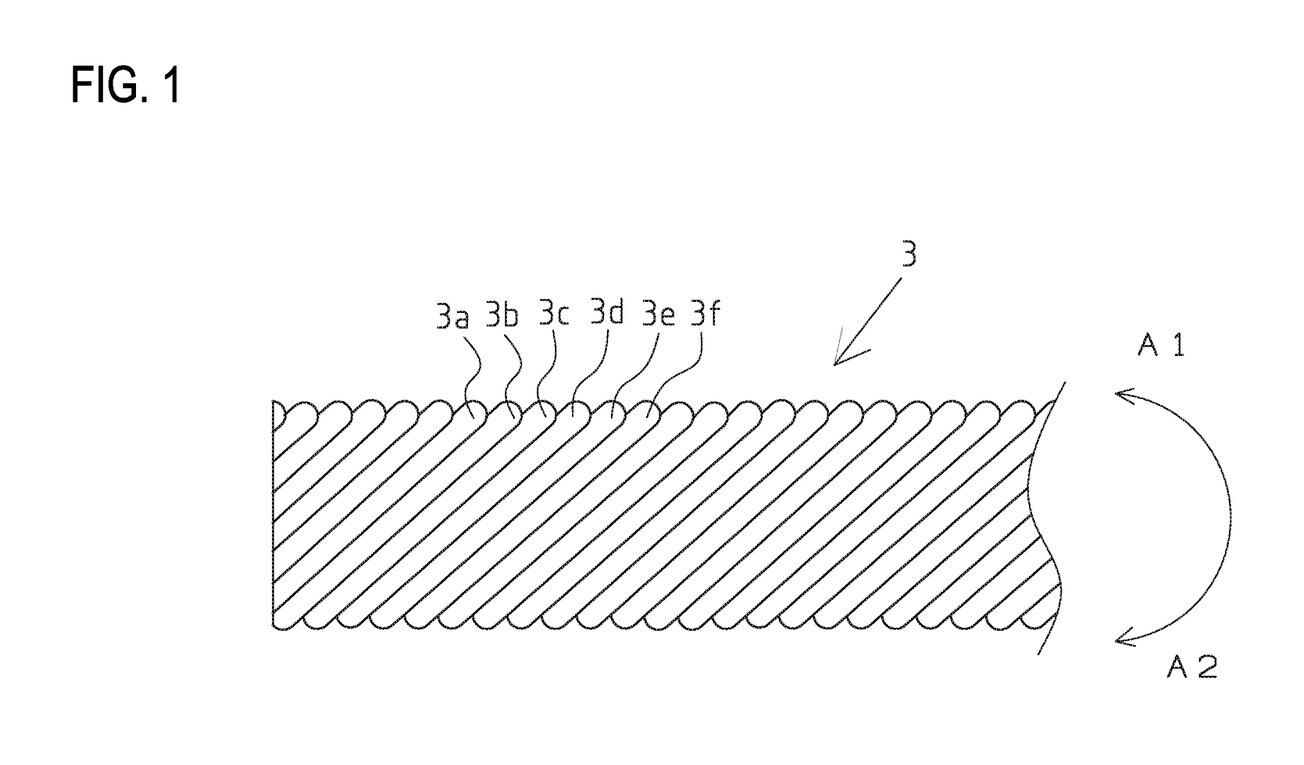
FIG. 1 is a side view of an inner multi-strand hollow body of a multilayer hollow body according to the disclosed embodiments.
Figure 2:
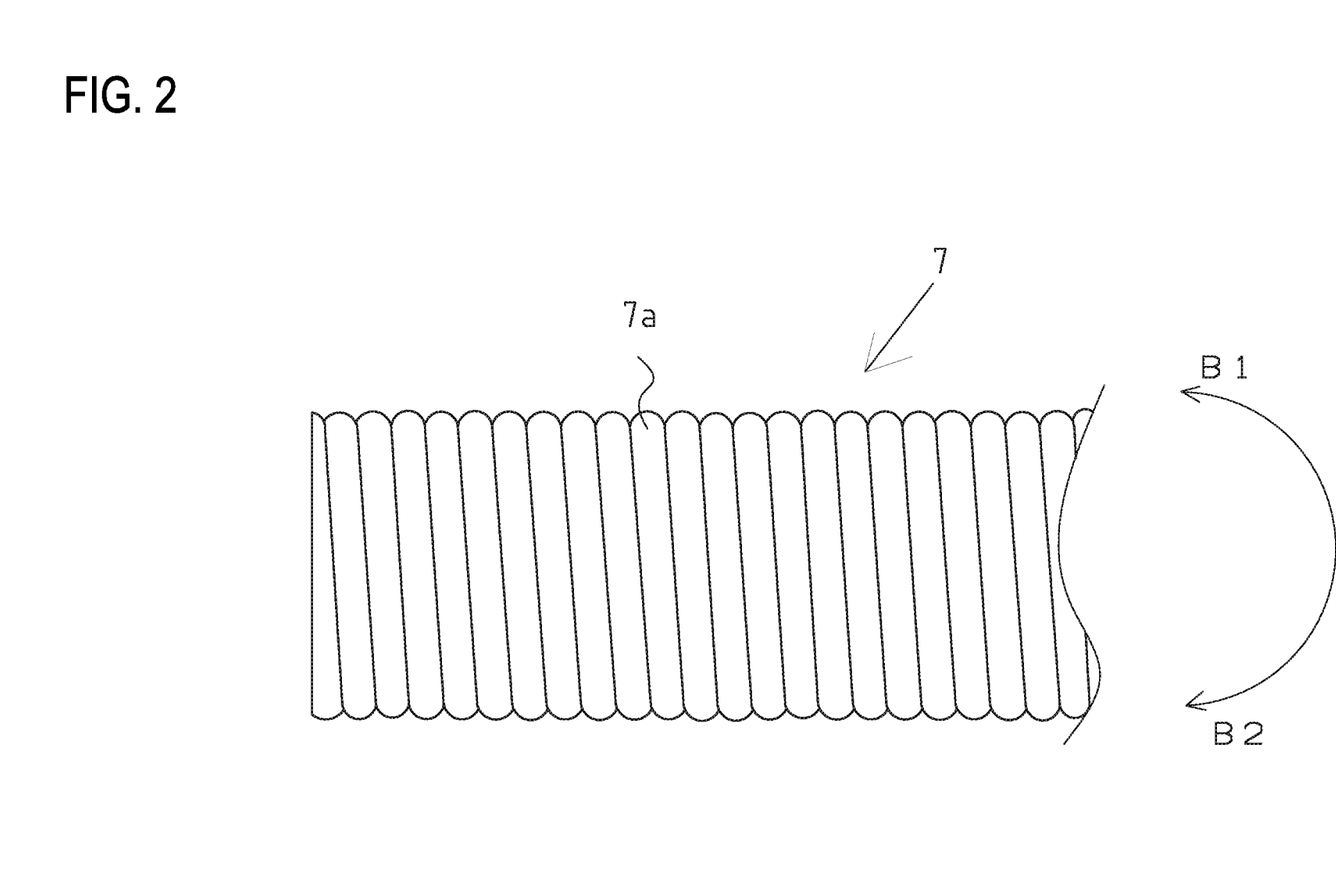
FIG. 2 is a side view of a single-strand hollow body of the multilayer hollow body according to the disclosed embodiments.
Figure 3:
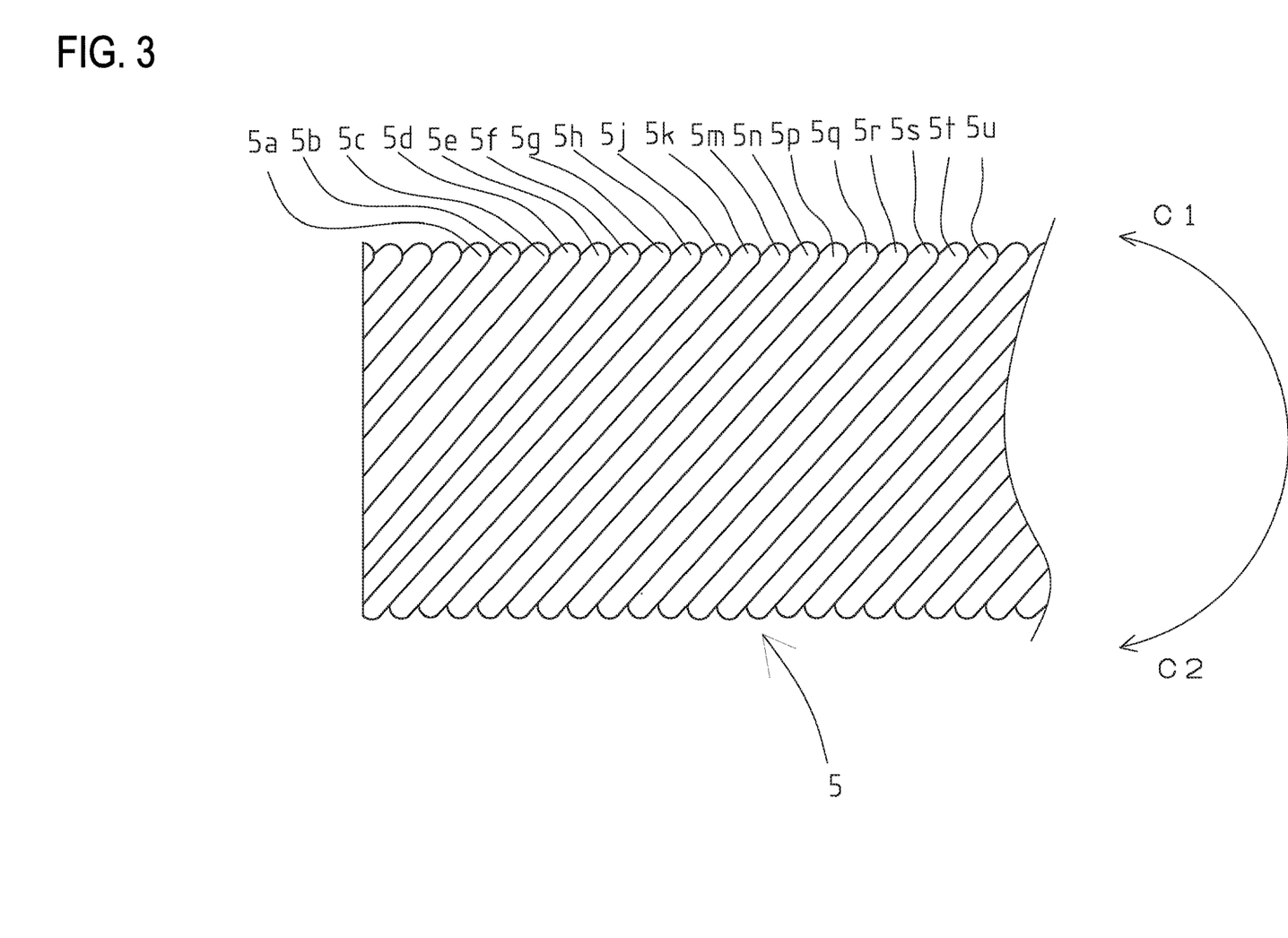
FIG. 3 is a side view of an outer multi-strand hollow body of the multilayer hollow body according to the disclosed embodiments.
Figure 4:
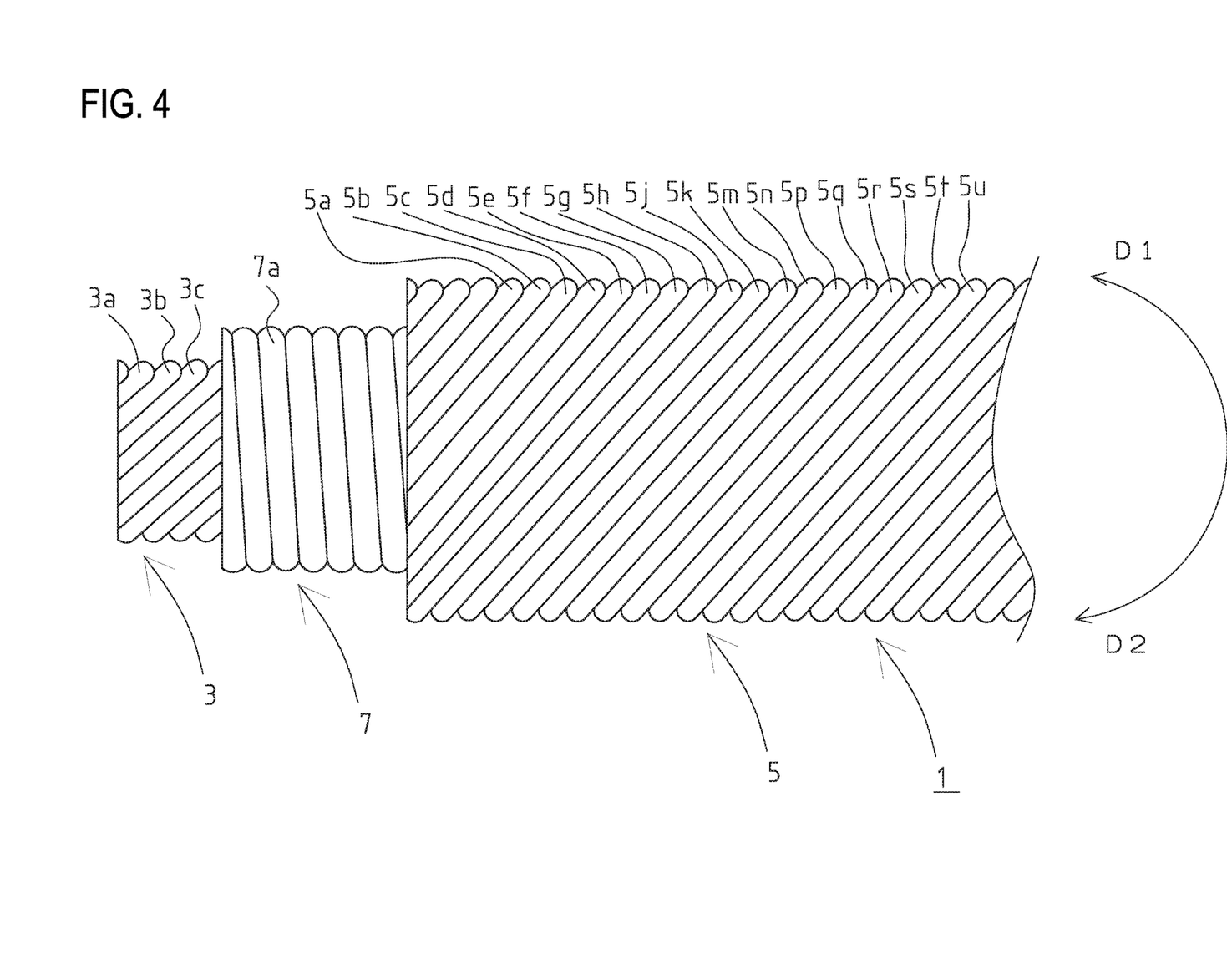
FIG. 4 is an explanatory diagram of the multilayer hollow body according to the disclosed embodiments.
Figure 5:
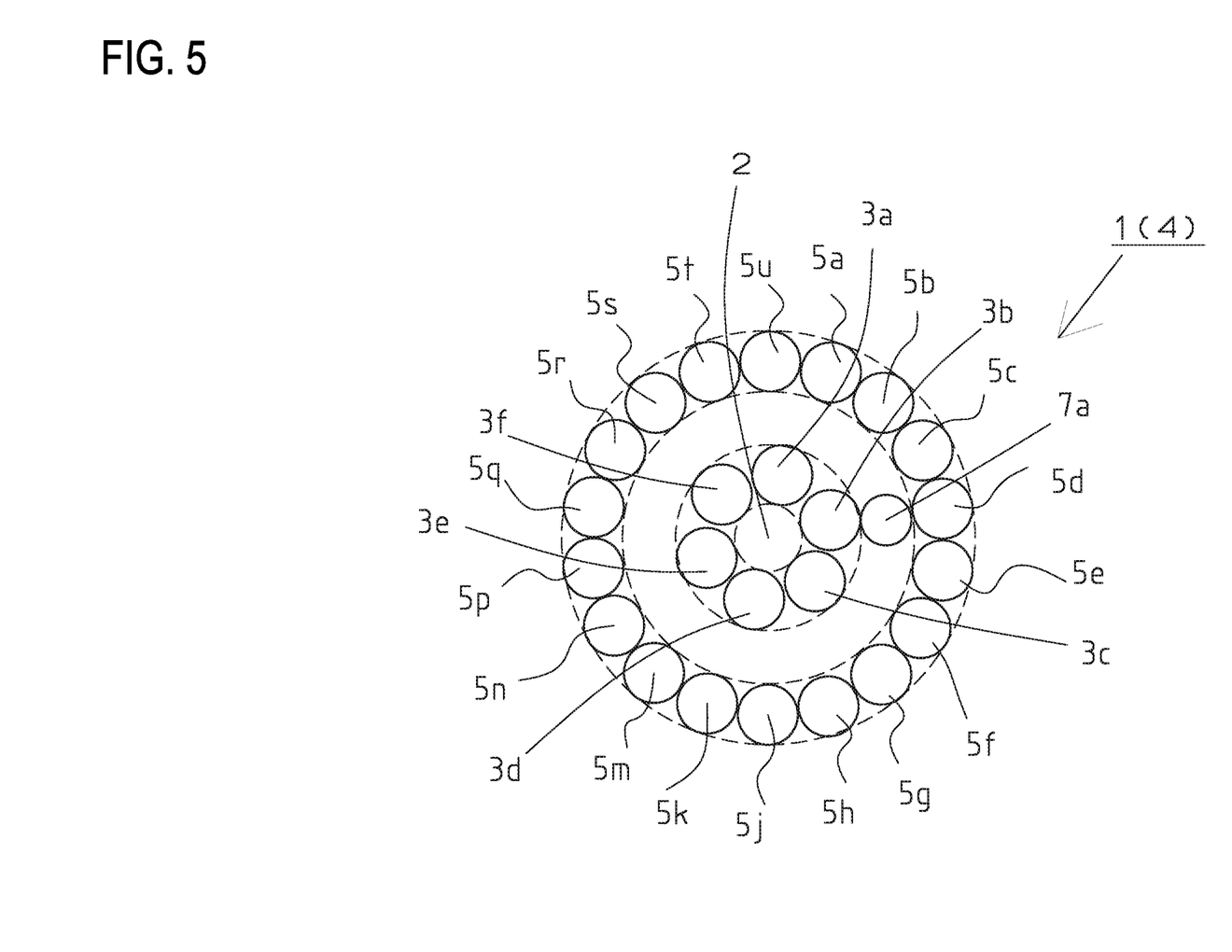
FIG. 5 is a cross-sectional explanatory diagram of the multilayer hollow body shown in FIG. 4.

FIG. 1 is a side view of an inner multi-strand hollow body of a multilayer body according to the disclosed embodiments. FIG. 2 is a side view of a single-strand hollow body of the multilayer body. FIG. 3 is a side view of an outer multi-strand hollow body of the multilayer body. FIG. 4 is an explanatory diagram of the multilayer body. FIG. 5 is a cross-sectional explanatory diagram of the multilayer body.

In FIG. 1, the inner multi-strand hollow body 3 is a coil body formed in a hollow form by twisting six element wires. To be more specific, the inner multi-strand hollow body 3 is formed in a hollow form by winding metal element wires 3a, 3b, 3c, 3d, 3e, 3f each formed of a stainless steel alloy.

Note that the inner multi-strand hollow body 3 shown in FIG. 1 is formed by twisting six element wires. However, the multi-strand hollow body 3 is not limited to being formed by twisting six element wires, as long as it is formed by twisting two or more element wires.

Moreover, the material of the element wire forming the inner multi-strand hollow body 3 is not limited to a stainless steel alloy, and may be other kinds of metal, e.g., tungsten, platinum, gold, or a resin.

Note that the metal element wires 3a, 3b, 3c, 3d, 3e, 3f forming the inner multi-strand hollow body 3 are wound in a counterclockwise direction (A2 direction in FIG. 1) toward the left side in the drawing (i.e., toward a distal end of the inner multi-strand hollow body 3).

In FIG. 2, a single-strand hollow body 7 is a coil body formed in a hollow form by twisting only one element wire. To be more specific, the single-strand hollow body 7 is formed by winding a metal element wire 7a formed of a stainless steel alloy.

Note that the material of the element wire forming the single-strand hollow body 7 is not limited to a stainless steel alloy, and may be other kinds of metal (e.g., tungsten, platinum, or gold) or a resin.

Note that the metal element wire 7a forming the single-strand hollow body 7 is wound in a clockwise direction (B1 direction in FIG. 2) toward the left side in the drawing (i.e., toward a distal end of the single-strand hollow body 7).

In FIG. 3, an outer multi-strand hollow body 5 is a coil body formed in a hollow form by twisting 18 element wires, similarly to the inner multi-strand hollow body 3. To be more specific, the outer multi-strand hollow body 5 is formed by winding metal element wires 5a, 5b, 5c, 5d, 5e, 5f, 5g, 5h, 5j, 5k, 5m, 5n, 5p, 5q, 5r, 5s, 5t, 5u each formed of stainless steel alloy.

The outer multi-strand hollow body 5 shown in FIG. 3 is formed by twisting 18 element wires. However, the outer multi-strand hollow body 5 is not limited to being formed by twisting 18 element wires, and it may be formed by twisting two or more element wires as long as it covers the single-strand hollow body 7. The material of the element wire forming the outer multi-strand hollow body 5 is not limited to a stainless steel alloy, and may be other kinds of metals, (e.g., tungsten, platinum, or gold) or a resin.

Note that the metal element wires 5a, 5b, 5c, 5d, 5e, 5f, 5g, 5h, 5j, 5k, 5m, 5n, 5p, 5q, 5r, 5s, 5t, 5u forming the outer multi-strand hollow body 5 are wound in a counterclockwise direction (C2 direction in FIG. 3) toward the left side in the drawing (i.e., toward a distal end of the outer multi-strand hollow body 5).

FIG. 4 is an explanatory diagram explaining a multilayer hollow body 1 that includes the inner multi-strand hollow body 3, the single-strand hollow body 7, and the outer multi-strand hollow body 5. In FIG. 4, the inner multi-strand hollow body 3 and the outer multi-strand hollow body 5 are wound in the same direction (D2 direction in FIG. 4), and the single-strand hollow body 7 is wound in an opposite direction to the inner multi-strand hollow body 3 and the outer multi-strand hollow body 5 (D1 direction in FIG. 4).

Moreover, in FIG. 4, a twisting angle (an angle relative to an axis perpendicular to the longitudinal axis) of the outer multi-strand hollow body 5 is larger than a twisting angle of the inner multi-strand hollow body 3, and a twisting angle of the single-strand hollow body 7 is larger than the twisting angle of the outer multi-strand hollow body 5.

FIG. 5 is a cross-sectional explanatory diagram of the multilayer hollow body 1, and illustrates that the outer multi-strand hollow body 5 is formed of the 18 metal element wires 5a, 5b, 5c, 5d, 5e, 5f, 5g, 5h, 5j, 5k, 5m, 5n, 5p, 5q, 5r, 5s, 5t, 5u, the inner multi-strand hollow body 3 is formed of the six metal element wires 3a, 3b, 3c, 3d, 3e, 3f, and the single-strand hollow body 7 is formed of only the one metal element wire 7a.

Note that although the multilayer hollow body 1 has been described above, an element wire 2 can be arranged inside the inner multi-strand hollow body 3 of FIG. 5 to form a solid multilayer body 4 (not having an inner hollow).

Note that a "multilayer body" is a concept including a "hollow multi layer body (multilayer hollow body)" and a "solid multilayer body," and thus is a wider concept than the "multilayer hollow body."

Moreover, in the multilayer body 4 in FIG. 5, one element wire 2 is arranged in the center. However, the center is not limited to including only one element wire, and may include a plurality of element wires or a stranded wire formed by twisting a plurality of element wires.

Next, the reason Why the rotational torque transmissibility of the multilayer hollow body 1 is improved will be described with reference to FIG. 1 to FIG. 5.

As described above, in the inner multi-strand hollow body 3 and the outer multi-strand hollow body 5, the metal element wires are wound in a counterclockwise direction (A2 direction in FIG. 1, C2 direction in FIG. 3) toward the distal end. In the single-strand hollow body 7, the metal element wire is wound in a clockwise direction (B1 direction in FIG. 2) toward the distal end.

1. Case of rotating a proximal end of the multilayer hollow body 1 in a clockwise direction (D1 direction in FIG. 4).

In the inner multi-strand hollow body 3, the metal element wires are wound in a counterclockwise direction (A2 direction in FIG. 1) toward the distal end. Thus, when the proximal end of the inner multi-strand hollow body 3 is rotated in a clockwise direction (A1 direction in FIG. 1), an outer diameter of the inner multi-strand hollow body 3 decreases.

Also in the outer multi-strand hollow body 5, the metal element wires are wound in a counterclockwise direction (C2 direction in FIG. 3) toward the distal end. Thus, when a proximal end of the outer multi-strand hollow body 5 is rotated in a clockwise direction (C1 direction in FIG. 3), an outer diameter of the outer multi-strand hollow body 5 decreases.

By contrast, in the single-strand hollow body 7, the metal element wire is wound in a clockwise direction (B1 direction in FIG. 2) toward the distal end. Thus, when a proximal end of the single-strand hollow body 7 is rotated in a clockwise direction (B1 direction in FIG. 2), an outer diameter of the single-strand hollow body 7 increases. However, the single-strand hollow body 7 is formed of a single strand with a large twisting angle, and thus an amount by which the outer diameter increases when one end is rotated is small.

Here, the multilayer hollow body 1 illustrated in FIG. 4 will be referred to.

In FIG. 4, when the proximal end of the multilayer hollow body 1 including the inner multi-strand hollow body 3, the single-strand hollow body 7, and the outer multi-strand hollow body 5 is rotated in a clockwise direction (D1 direction in FIG. 4), the outer diameter of the inner multi-strand hollow body 3 decreases, the outer diameter of the single-strand hollow body 7 increases, and the outer diameter of the outer multi-strand hollow body 5 decreases. Consequently, the adhesion between the single-strand hollow body 7 and the outer multi-strand hollow body 5 is increased.

Meanwhile, when the proximal end of the multilayer hollow body 1 is rotated in a clockwise direction (D1 direction in FIG. 4), the outer diameter of the inner multi-strand hollow body 3 decreases, and the outer diameter of the single-strand hollow body 7 increases, so that a space between inner multi-strand hollow body 3 and the single-strand hollow body 7 increases. However, the single-strand hollow body 7 is of a single strand with a large twisting angle, and thus an amount by which the space increases is small.

Therefore, when the proximal end of the multilayer hollow body 1 is rotated in a clockwise direction (D1 direction in FIG. 4), it is possible to improve the rotational torque transmissibility to the distal end of the multilayer hollow body 1.

2. Case of rotating a proximal end of the multilayer hollow body 1 in a counterclockwise direction.

In the inner multi-strand hollow body 3, the metal element wires are wound in a counterclockwise direction (A2 direction in FIG. 1) toward the distal end. Thus, when the proximal end of the inner multi-strand hollow body 3 is rotated in a counterclockwise direction (A2 direction in FIG. 1), an outer diameter of the inner multi-strand hollow body 3 increases.

Also in the outer multi-strand hollow body 5, the metal element wires are wound in a counterclockwise direction (C2 direction in FIG. 3) toward the distal end. Thus, when the proximal end of the outer multi-strand hollow body 5 is rotated in a counterclockwise direction (C2 direction in FIG. 3), an outer diameter of the outer multi-strand hollow body 5 increases.

Meanwhile, in the single-strand hollow body 7, the metal element wire is wound in a clockwise direction (B1 direction in FIG. 2) toward the distal end. Thus, when the proximal end of the single-strand hollow body 7 is rotated in a counterclockwise direction (B2 direction in FIG. 2), an outer diameter of the single-strand hollow body 7 decreases. However, the single-strand hollow body 7 is formed of a single strand with a large twisting angle, and thus an amount by which the outer diameter reduces when one end is rotated is small.

Here, the multilayer hollow body 1 illustrated in FIG. 4 will be referred to.

In FIG. 4, when the proximal end of the multilayer hollow body 1 including the inner multi-strand hollow body 3, the single-strand hollow body 7, and the outer multi-strand hollow body 5 is rotated in a counterclockwise direction (D2 direction in FIG. 4), the outer diameter of the inner multi-strand hollow body 3 increases, the outer diameter of the single-strand hollow body 7 decreases, and the outer diameter of the outer multi-strand hollow body 5 increases. Consequently, the adhesion between the single-strand hollow body 7 and the inner multi-strand hollow body 3 is increased.

Meanwhile, when the proximal end of the multilayer hollow body 1 is rotated in a counterclockwise direction (D2 direction in FIG. 4), the outer diameter of the outer multi-strand hollow body 5 increases, and the outer diameter of the single-strand hollow body 7 decreases, so that the space between the outer multi-strand hollow body 5 and the single-strand hollow body 7 increases. However, the single-strand hollow body 7 is of a single strand with a large twisting angle, and thus an amount by which the space increases is small.

Therefore, when the proximal end of the multilayer hollow body 1 is rotated in a counterclockwise direction (D2 direction in FIG. 4), it is possible to improve rotational torque transmissibility to the distal end of the multilayer hollow body 1.

Note that a reason why the rotational torque transmissibility of the multilayer body 4 is improved is the same as the above-described reason as to why the rotational torque transmissibility of the multilayer hollow body 1 is improved, and thus the explanation thereof is omitted.

With the multilayer hollow body 1 and the multilayer body 4, the adhesion between the single-strand hollow body 7 and the inner multi-strand hollow body 3 is increased, and the space between the single-strand hollow body 7 and the outer multi-strand hollow body 5 is reduced as much as possible; or the adhesion between the single-strand hollow body 7 and the outer multi-strand hollow body 5 is increased, and the space between the single-strand hollow body 7 and the inner multi-strand hollow body 3 is reduced as much as possible. As a result, when one end of the multilayer hollow body 1 and the multilayer body 4 is rotated in either a clockwise direction or a counterclockwise direction, it is possible to improve rotational torque transmissibility to the other end of the multilayer hollow body Note that the multilayer hollow body 1 is a three-layer hollow body including the inner multi-strand hollow body 3 and the outer multi-strand hollow body 5 wound in a same direction, and the single-strand hollow body 7 arranged between the inner multi-strand hollow body 3 and the outer multi-strand hollow body 5 and wound in an opposite direction from the inner multi-strand hollow body 3 and the outer multi-strand hollow body 5. However, the multilayer hollow body 1 is not limited to a three-layer hollow body, and the multilayer hollow body may be formed of four or more layers.

However, it is necessary for the multilayer hollow body 1 to include at least a one single-strand hollow body, and two multi-strand hollow bodies that are disposed adjacently to the inner side and the outer side of the single-strand hollow body and that are wound in an opposite direction from the single-strand coil.

Moreover, even when the multilayer hollow body includes a plurality of the above-described three-layer structure, the same effects are exerted.

Moreover, the multilayer body 4 is a four-layer solid body including one element wire 2, the inner multi-strand hollow body 3 and the outer multi-strand hollow body 5 wound in a same direction, and the single-strand hollow body 7 arranged between the inner multi-strand hollow body 3 and the outer multi-strand hollow body 5 and wound in an opposite direction from the inner multi-strand hollow body 3 and the outer multi-strand hollow body 5. However, the multilayer body 4 is not limited to a four-layer solid body, and may include five or more-layers.

However, it is necessary for the multilayer body 4 to include at least a three-layer hollow body including at least a one-strand single-strand hollow body, and two multi-strand hollow bodies that are disposed adjacently to the inner side and the outer side of the single-strand hollow body with winding in an opposite direction from the one-strand single-strand coil.

Moreover, even when the multilayer body includes a plurality of the above-described three-layer structure, the same effects are exerted.

Figure 6:
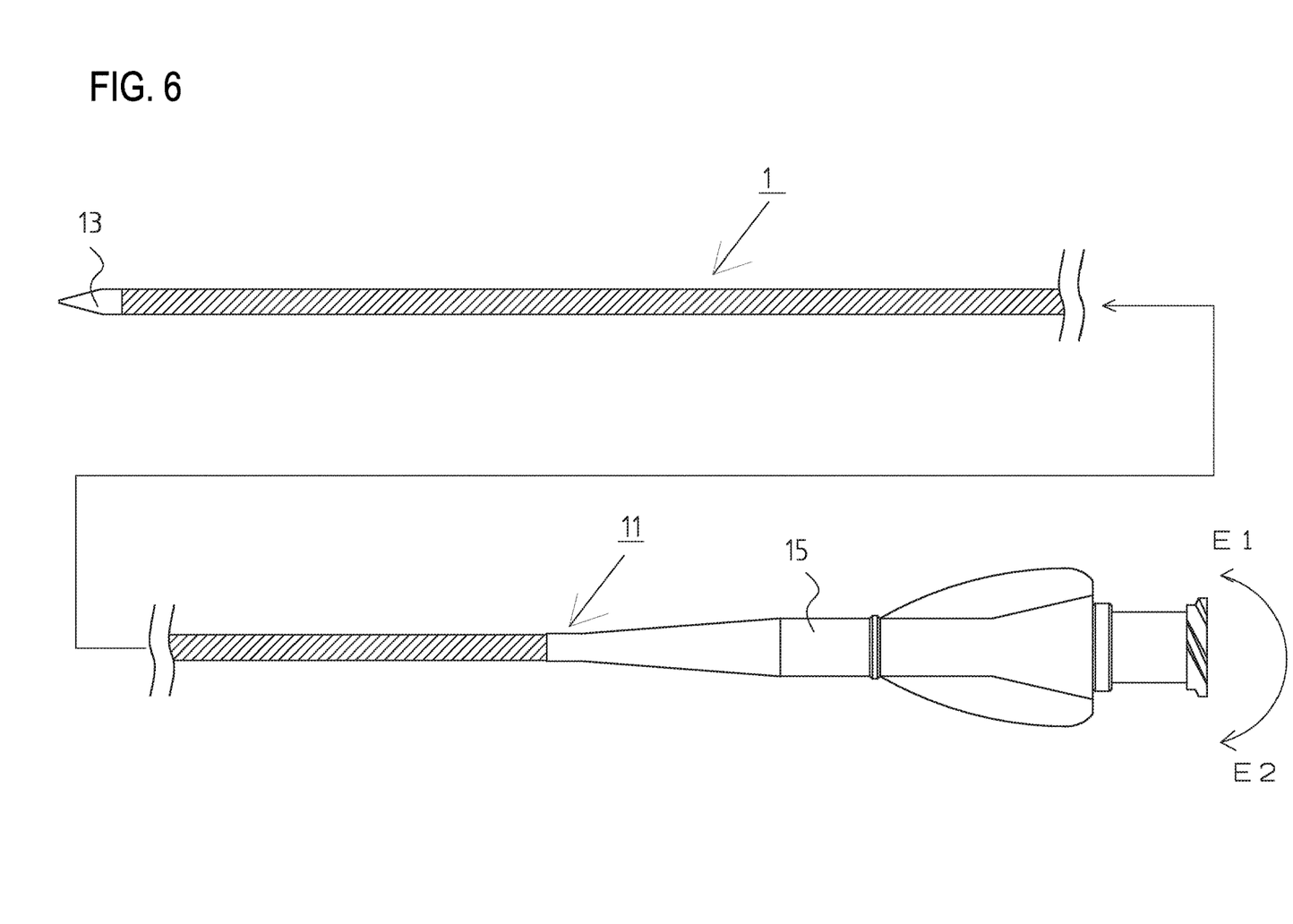
FIG. 6 is a schematic side view of a catheter according to the disclosed embodiments.

FIG. 6 is a schematic side view of a catheter according to the disclosed embodiments.

In FIG. 6, a catheter 11 includes the multilayer hollow body 1, a distal end tip 13 connected to a distal end of the multilayer hollow body 1, and a connector 15 connected to a proximal end of the multilayer hollow body 1.

Note that regarding the multilayer hollow body 1 used in the catheter 11, various configurations can be used, as described above.

The distal end tip 13 includes a lumen (not illustrated) that communicates with to a lumen of the multilayer hollow body 1. The distal end tip 13 has a tapered form and is thinner toward the distal end.

The material of the distal end tip 13 is a metal, a resin, or the like, and is not particularly limited. However, it is preferably metal when the material of the multilayer hollow body 1 is metal. In this way, the distal end tip 13 and the multilayer hollow body 1 can be joined firmly by welding.

Moreover, the connector 15 also has a lumen that communicates with the lumen of the multilayer hollow body 1. The material of the connector 15 is not particularly limited. However, it is normally formed of a resin.

The catheter 11 includes the multilayer hollow body 1. Thus, when the connector 15 is rotated in a counterclockwise direction (E2 direction in FIG. 6), the adhesion between the single-strand hollow body 7 and the inner multi-strand hollow body 3 is increased, and the space between the single-strand hollow body 7 and the outer multi-strand hollow body 5 is reduced as much as possible, whereby it is possible to improve torque transmissibility to the distal end tip 13 of the catheter 11.

Moreover, when the connector 15 is rotated in a clockwise direction (E1 direction in FIG. 6), the adhesion between the single-strand hollow body 7 and the outer multi-strand hollow body 5 is increased, and the space between the single-strand hollow body 7 and the inner multi-strand hollow body 3 is reduced as much as possible, whereby it is possible to improve torque transmissibility to the distal end tip 13 of the catheter 11.

Figure 7:
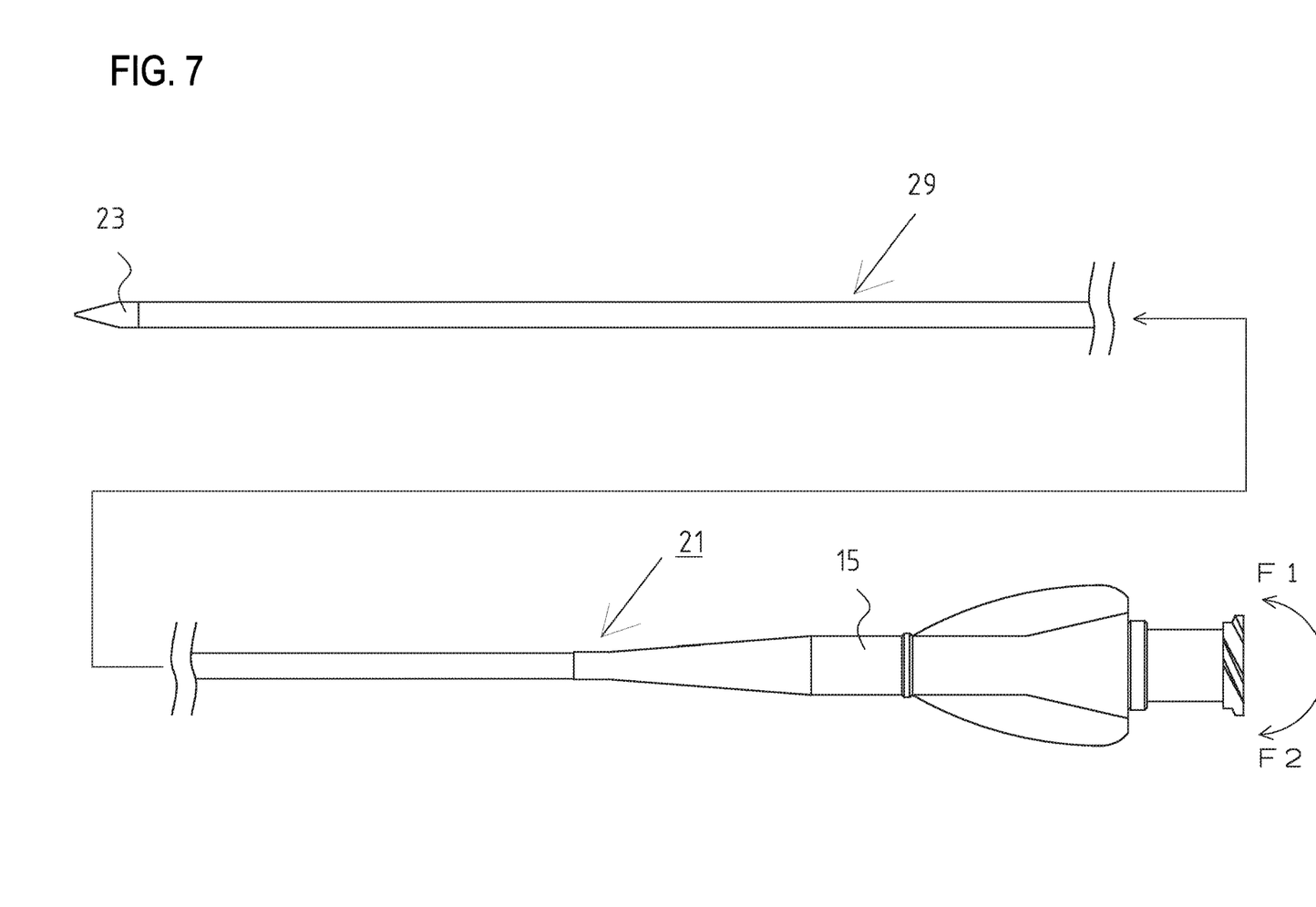
FIG. 7 is a schematic side view of a catheter according to the disclosed embodiments.
Figure 8:
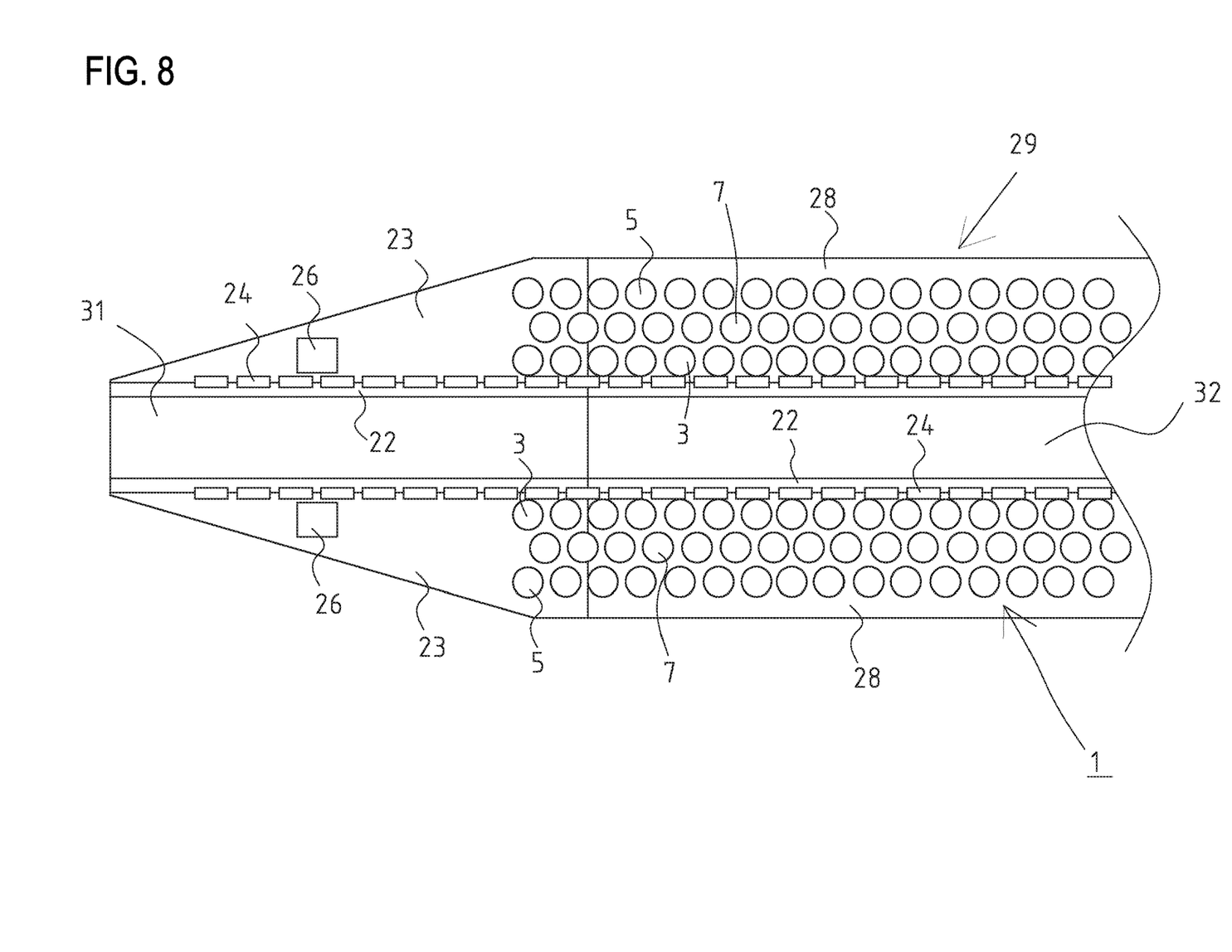
FIG. 8 is a cross-sectional view of a distal end of the catheter shown in FIG. 7.

FIG. 7 is a schematic side view of a catheter according to a the disclosed embodiments. FIG. 8 is a cross-sectional view of a distal end of the catheter.

In FIG. 7, a catheter 21 includes a catheter main body 29, a distal end tip 23 connected to a distal end of the catheter main body 29, and the connector 15 connected to a proximal end of the catheter main body 29.

The catheter main body 29 includes, as illustrated in FIG. 8, an inner layer 22 that is a hollow cylindrical body having a lumen 32, a braid 24 covering an outer periphery of the inner layer 22, the multilayer hollow body 1 covering the braid 24, and an outer layer 28 covering the multilayer hollow body 1.

Note that regarding the multilayer hollow body 1 used in the catheter 21, various configurations can be used, as described above.

The distal end tip 23 includes a lumen 31 that communicates with the lumen 32 of the multilayer hollow body 1, The distal end tip 23 has a tapered form and is thinner toward the distal end.

The material of the distal end tip 23 is not particularly limited. However, a material formed of a resin that is softer than the catheter main body 29 is preferably used.

Note that the inner layer 22 and the braid 24 extend to the distal end of the distal end tip 23 from the catheter main body 29. Moreover, the multilayer hollow body 1 also extends into the distal end tip 23 from the catheter main body 29.

Moreover, in the distal end tip 23, a marker 26 formed of a radiopaque material is disposed.

Furthermore, the connector 15 also has a lumen that communicates with the lumen 32 of the multilayer hollow body 1. The material of the connector 15 is not particularly limited. However, it is normally formed of a resin.

The catheter 21 includes the multilayer hollow body 1, and the multilayer hollow body 1 protrudes into the inside of the distal end tip 23. Thus, when the connector 15 is rotated in a counterclockwise direction (F2 direction in FIG. 7), the adhesion between the single-strand hollow body 7 and the inner multi-strand hollow body 3 is increased, and the space between the single-strand hollow body 7 and the outer multi-strand hollow body 5 is reduced as much as possible, whereby it is possible to improve torque transmissibility to the distal end tip 23 of the catheter 21.

Moreover, when the connector 15 is rotated in a clockwise direction (F1 direction in FIG. 7), the adhesion between the single-strand hollow body 7 and the outer multi-strand hollow body 5 is increased, and the space between the single-strand hollow body 7 and the inner multi-strand hollow body 3 is reduced as much as possible, whereby it is possible to improve torque transmissibility to the distal end tip 23 of the catheter 21.

A multilayer body, a multilayer hollow body, and a catheter according to the disclosed embodiments have been described above. However, the invention is not limited to the above-described embodiments, and can be implemented with various changes.

For example, in the above-described embodiments, the element wires forming the multi-strand body and the multi-strand hollow body are element wires with a round cross section. However, the element wires may have a substantially rectangular section. However, when the multilayer body itself or the multilayer hollow body itself appears on an outer surface, the element wire with a round cross section is preferable from the viewpoint of preventing the outer periphery from catching on other surfaces.

What is claimed is:

1. A multilayer body comprising:
   a single-strand hollow body that is a coil body formed by winding only one element wire;
   an inner multi-strand hollow body that is disposed adjacently to an inner periphery of the single-strand hollow body and that is a coil body formed by winding a plurality of element wires in an opposite direction from the single-strand hollow body; and
   an outer multi-strand hollow body that is disposed adjacently to an outer periphery of the single-strand hollow body and that is a coil body formed by winding a plurality of element wires in an opposite direction from the single-strand hollow body
   wherein at a longitudinal position of the multilayer body, a twisting angle of the single-strand hollow body is larger than a twisting angle of the inner multi-strand hollow body and a twisting angle of the outer multi-strand hollow body, and the twisting angle of the outer multi-strand hollow body is larger than the twisting angle of the inner multi-strand hollow body.

2. The multilayer body according to claim 1, further comprising:
   a braid that is disposed adjacently to an inner periphery of the inner multi-strand hollow body.

3. The multilayer body according to claim 2, further comprising:
   an inner layer that is disposed adjacently to an inner periphery of the braid; and
   an outer layer that covers the inner layer, the braid, the single-strand hollow body, the inner multi-strand hollow body, and the outer multi-strand hollow body.

4. A catheter, comprising:
the multilayer body according to claim 1;
a distal end tip that is connected to a distal end of the multilayer body; and
a connector that is connected to a proximal end of the multilayer body.

5. A catheter comprising:
an inner layer;
the multilayer body according to claim 1 disposed on an outer periphery of the inner layer;
an outer layer that covers the inner layer and the multilayer body;
a distal end tip that is connected to a distal end of the inner layer and a distal end of the outer layer, wherein a distal end of the multilayer body protrudes into the distal end tip; and
a connector that is connected to a proximal end of the inner layer, a proximal end of the outer layer, and a proximal end of the multilayer body.

\* \* \* \* \*